United States Patent [19]

Tatton

[11] Patent Number: 5,783,606
[45] Date of Patent: Jul. 21, 1998

[54] DEPRENYL COMPOUNDS FOR TREATMENT OF GLAUCOMA

[75] Inventor: William G. Tatton, Halifax, Canada

[73] Assignee: The University of Toronto Innovations Foundation, Toronto, Canada

[21] Appl. No.: 598,845

[22] Filed: Feb. 9, 1996

Related U.S. Application Data

[63] Continuation-in-part of Ser. No. 515,893, Aug. 16, 1995, abandoned, which is a continuation of Ser. No. 394,003, Feb. 10, 1995, abandoned.

[51] Int. Cl.⁶ .................................................. A61K 31/135
[52] U.S. Cl. ........................... 514/649; 514/654; 514/913
[58] Field of Search .................................. 514/649, 654, 514/913

[56] References Cited

U.S. PATENT DOCUMENTS 5,322,859  6/1994  Schoenwald et al. .................. 514/649

FOREIGN PATENT DOCUMENTS

WO17169  10/1992  Canada.

*Primary Examiner*—Zohreh Fay
*Attorney, Agent, or Firm*—Lahive & Cockfield, LLP

[57] ABSTRACT

Methods and kits for treatment of glaucoma are disclosed. In general, the methods of the invention include administering a therapeutically effective amount of a deprenyl compound to a subject such that the subject is treated for glaucoma.

19 Claims, 3 Drawing Sheets

DEPRENYL COMPOUNDS FOR TREATMENT OF GLAUCOMA

RELATED APPLICATIONS

This application is a continuation-in-part of U.S. Ser. No. 08/515,893, entitled "A Method of Treating Optical Nerve Damage with Deprenyl", filed on Aug. 16, 1995 now abandoned, which is a continuation of U.S. Ser.. No. 08/394,003, entitled "A Method of Treating Optical Nerve Damage with Deprenyl", filed on Feb. 10, 1995, now abandoned. The methods of this application also can involve compounds and/or compositions described in U.S. Pat. No. 5,449,095, and a co-pending application entitled "Use of Deprenyl Compounds to Maintain, Prevent Loss, or Recover Nerve Cell Function", filed on even date herewith. The contents of all of the aforementioned applications and issued patents are hereby expressly incorporated by reference.

BACKGROUND OF THE INVENTION

Glaucoma is a disease of the eye characterized by elevated intraocular pressure. The elevated intraocular pressure leads to hardening of the eyeball, narrowing of the field of vision and a decrease in a subject's visual acuity. Glaucoma is a disease of the optic nerve and the elevated eye pressures are related to damage of this nerve. The optic nerve carries images from the retina to the brain. Glaucoma damages optical nerve cells causing blindspots to occur within a subject's vision. These blind spots typically are not noticed by the subject until considerable damage to the optic nerve has already occurred. The terminal stage of glaucoma is total blindness of the subject.

Approaches to treating glaucoma include the topical application of cholinergic agents, e.g., pilocarpine, alpha- or beta- adrenergic agonists or antagonists, e.g., clonidine, timolol or epinephrine. An alternative approach for treating glaucoma is the systemic administration of carbonic anhydrase inhibitors. In some cases laser or operative surgery is used to treat glaucoma.

Problems exist with the aforementioned approaches to treating glaucoma in that the treatments can be accompanied by side-effects. For example the instillation of a cholinergic agent, such as pilocarpine, into the eye of a subject can cause nausea, diarrhea, muscular spasms, sweating, lacrimation, salivation, etc. Contraction of the pupil (myosis) and of the ciliary muscle of the eye, as well as dilation of the blood vessels of the iris and conjunctiva also can be observed. Visual complications, e.g., spasm of accommodation, myopia or a decrease in visual acuity, also can occur.

The treatment with a sympathomimetic agent such as dipivalylepinephrine is known frequently to produce sensations of burning or irritation in a subject. Another side-effect of these agents is the appearance of cardiac disturbances, e.g., palpitations, tachycardia, arrythmia, etc.

Clonidine, which is known as an alpha-2-adrenergic receptor agonist, can bring about mydriasis, as well as an initial phase of ocular hypertension (biphasic effect). Furthermore, in spite of the topical application of the product to the eye, important systemic effects, such as bradycardia and hypotension, have been observed.

The use of beta-blocking medicaments also can cause important systemic effects after topical administration to the eye, due to the absence of a "first pass effect". Timolol, for example, causes bradycardia or hypotension. These systemic secondary reactions to beta-blocking medicaments can reach such a severe level that the treatment has to be discontinued. Cases of suicidal depression, hallucinations, nightmares or psychoses requiring hospitalization have been reported in connection with these medicaments. Furthermore, these compounds have to be administered with extreme precautions to patients subject to cardiac or pulmonary functional disorders. In such patients, amongst others, cases of arrhythmia, cardiac arrest, asthma, dyspnea and bronchospasms have been reported.

The treatment with a sympatholytic agent, such as guanethidine, causes hyperemia of the conjunctiva and some irritation, not to mention the fact that these agents only have a low tendency to reduce intraocular pressure.

Finally, in the treatment of glaucoma with carbonic anhydrase inhibitors, such as acetazolamide or methazolamide, serious systemic side-effects, such as depression of the central nervous system, weight loss and, mainly, bone marrow hypofunction, have been reported.

The use of conventional hypotensive agents for the treatment of glaucoma is accompanied by considerable risks. Known medications are not particularly well suited for topical treatment and the systemic side-effects of these medicaments make them delicate to use because these effects are far from being negligible and because they can have, in some cases, severe consequences.

SUMMARY OF THE INVENTION

This invention provides methods and kits useful for the treatment of glaucoma. In one aspect, the methods of the invention include administering a therapeutically effective amount of a deprenyl compound to a subject such that the subject is treated for glaucoma. In a preferred embodiment, the deprenyl compound is represented by the structure:

$$R_4-R_3-CH-N\begin{matrix}R_1\\ \\R_5-R_6\end{matrix}$$
$$\phantom{R_4-R_3-C}|\phantom{H-N}$$
$$\phantom{R_4-R_3-}R_2$$

in which $R_1$ is hydrogen, alkyl, alkenyl, alkynyl, aralkyl, alkylcarbonyl, arylcarbonyl, alkoxycarbonyl, or aryloxycarbonyl; $R_2$ is hydrogen or alkyl; $R_3$ is a single bond, alkylene, or $-(CH_2)_n-X-(CH_2)_m$ in which X is O, S, or N-methyl; m is 1 or 2, and n is 0, 1, or 2; $R_4$ is alkyl, alkenyl, alkynyl, heterocyclyl, aryl or aralkyl; $R_5$ is alkylene, alkenylene, alkynylene and alkoxylene; and $R_6$ is $C_3$–$C_6$ cycloalkyl or

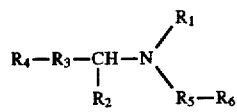
; or $R_2$ and $R_4$–$R_3$ are joined to form, together with the methine to which they are attached, a cyclic or polycyclic group; and pharmaceutically acceptable salts thereof. In preferred embodiments, $R_1$ is a group that can be removed in vivo; $R_1$ is hydrogen; $R_1$ is alkyl; $R_1$ is methyl; $R_2$ is methyl; $R_3$ is methylene; $R_4$ is aryl; or $R_4$ is phenyl. In still other preferred embodiments, $R_5$ is alkylene, more preferably methylene. In other preferred embodiments, $R_6$ is —C≡CH. In other preferred embodiments, $R_6$ is cyclopentyl.

In another embodiment, the deprenyl compound has the structure

3

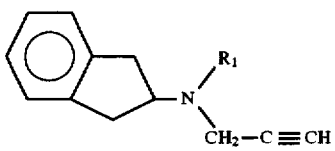

in which $R_1$ is hydrogen, alkyl, alkenyl, alkynyl, aralkyl, alkylcarbonyl, arylcarbonyl, alkoxycarbonyl, or aryloxycarbonyl.

In another preferred embodiment, the deprenyl compound is represented by the structure:

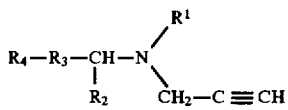

in which $R_1$ is hydrogen, alkyl, alkenyl, alkynyl, aralkyl, alkylcarbonyl, arylcarbonyl, alkoxycarbonyl, or aryloxycarbonyl; $R_2$ is hydrogen or alkyl; $R_3$ is a bond or methylene; and $R_4$ is aryl or aralkyl; or $R_2$ and $R_4$–$R_3$ are joined to form, together with the methine to which they are attached, a cyclic or polycyclic group; and pharmaceutically acceptable salts thereof.

In another embodiment, the deprenyl compound is represented by the structure:

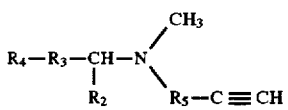

in which $R_2$ is hydrogen or alkyl; $R_3$ is a bond or methylene; and $R_4$ is aryl or aralkyl; or $R_2$ and $R_4$–$R_3$ are joined to form, together with the methine to which they are attached, a cyclic or polycyclic group; and $R_5$ is alkylene, alkenylene, alkynylene and alkoxylene; and pharmaceutically acceptable salts thereof.

In yet another embodiment, the deprenyl compound is represented by the structure:

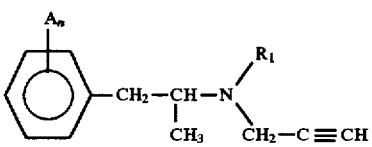

in which $R_1$ is hydrogen, alkyl, alkenyl, alkynyl, aralkyl, alkylcarbonyl, arylcarbonyl, alkoxycarbonyl, or aryloxycarbonyl; A is a substituent independently selected for each occurence from the group consisting of halogen, hydroxyl, alkyl, alkoxyl, cyano, nitro, amino, carboxyl, —$CF_3$, or azido; n is 0 or an integer from 1 to 5; and pharmaceutically acceptable salts thereof.

In other preferred embodiments, the deprenyl compound is (–)-deprenyl, (–)-pargyline, or (–)-desmethyldeprenyl.

In another aspect, tie invention provides a kit useful for the treatment of glaucoma. In one embodiment, the kit includes a container of a deprenyl compound and instructions for administering a therapeutically effective amount of the deprenyl compound to a subject such that the subject is treated for glaucoma.

DETAILED DESCRIPTION OF THE INVENTION

Figure 1:
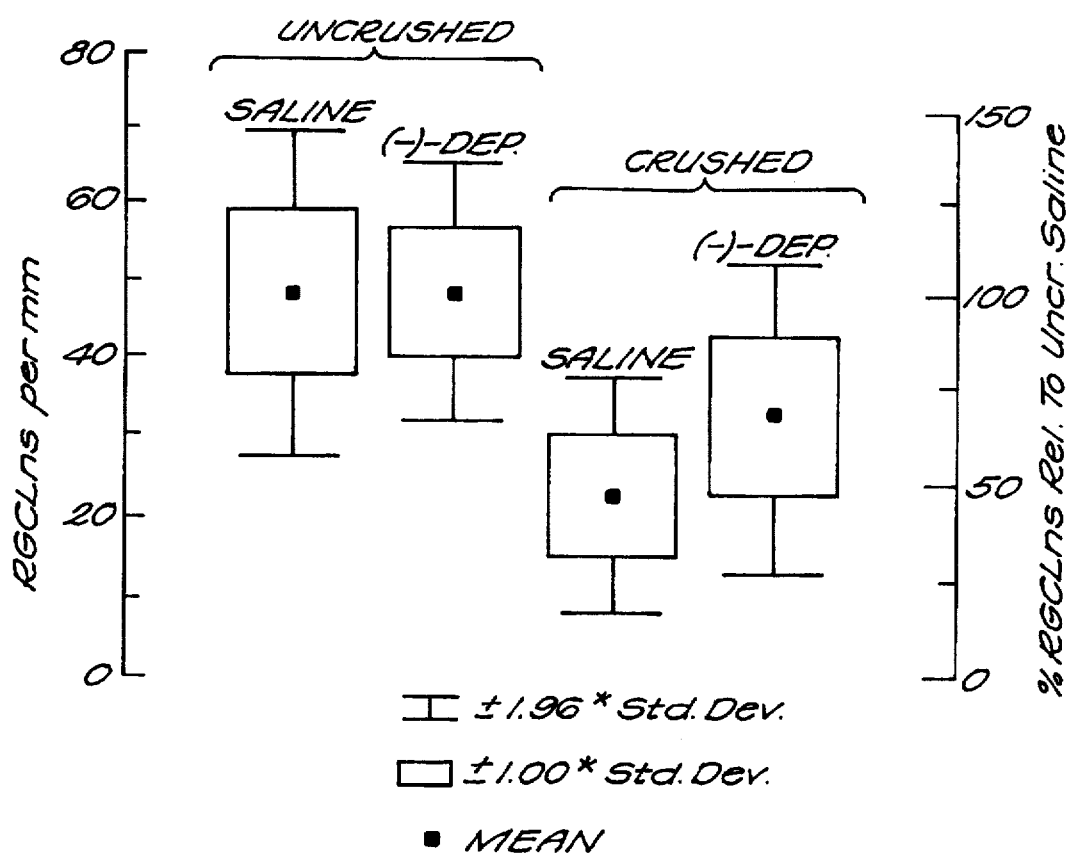
FIG. 1 is a box plot of the distributions of the counts of retinal ganglion cell layer neuronal cell bodies (RGCLncbs) for four experimental groups, showing that deprenyl treatment increases neuronal survival after optic nerve crush.
Figure 2A:
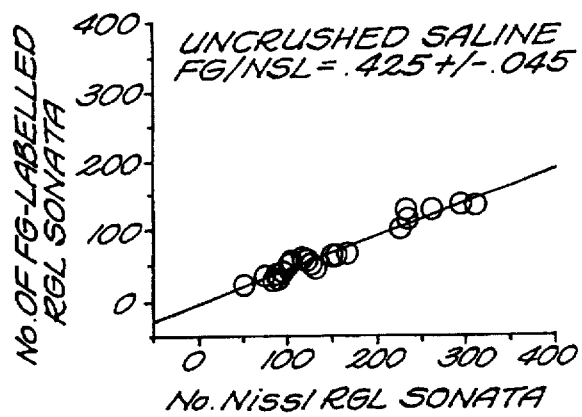
FIG. 2 shows a plot of counts of Nissl stained cell bodies and FG labelled cell bodies for varying lengths of retinal sections, showing that neuronal cell bodies in the retinal ganglion cell layer (RGCL) send axons to the SC.
Figure 2B:
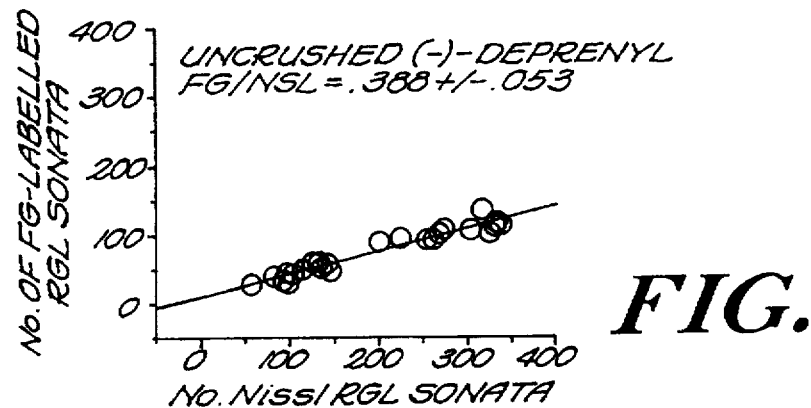
Figure 2C:
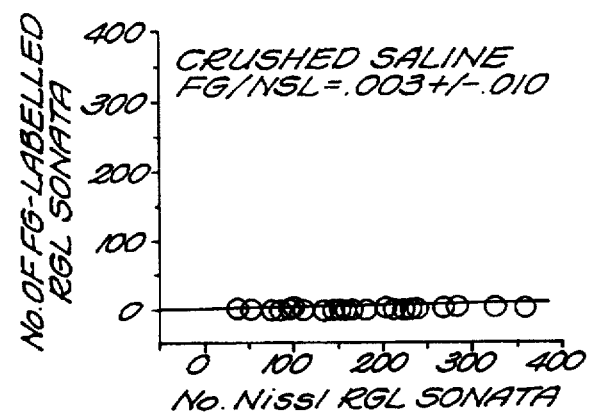
Figure 2D:
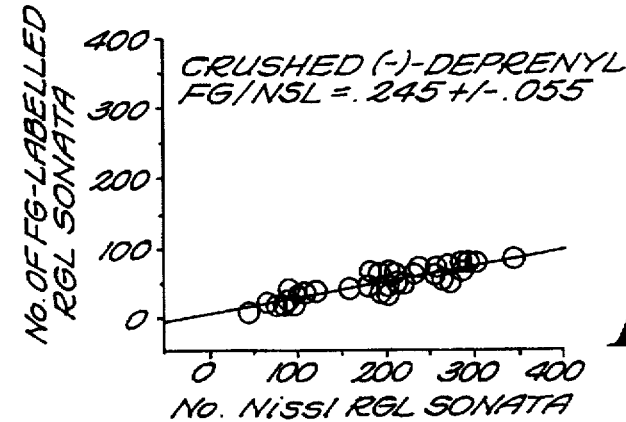

The present invention provides methods of treating glaucoma. In general, the methods include administering a therapeutically effective amount of a deprenyl compound to a subject in need thereof, such that the subject is treated for glaucoma.

The language "glaucoma" is art-recognized. The term includes both acute and chronic diseases of the eye characterized by elevated intraocular pressure. Symptoms of glaucoma include high pressure within the eyeball, hardening of the eyeball, narrowing of the field of vision, death of optic nerve cells, development of retinal blind spots, and decreased visual acuity.

The term "subject", as used herein, refers to a warm-blooded animal in need of treatment for, or susceptible to, glaucoma. In preferred embodiments, the subject is a mammal, including humans and non-human mammals such as dogs, cats, pigs, cows, sheep, goats, rats, and mice. In a particularly preferred embodiment, the subject is a human.

The language "therapeutically effective amount" of a deprenyl compound, as used herein, refers to an amount of a therapeutic compound sufficient to significantly ameliorate glaucoma or at least one symptom thereof in a subject. "Significant amelioration" includes elimination or substantial reduction in severity of one or more symptoms or diagnostic characteristics of glaucoma. A "substantial reduction" means at least about 5% reduction, more preferably at least about 10% reduction, and more preferably at least about 20% reduction in severity of one or more symptoms or diagnostic characteristics of glaucoma. Thus, a therapeutically effective amount of a therapeutic compound can decrease intraocular pressure, prevent or delay death of retinal or optic nerve cells, improve field of vision or visual acuity, or otherwise ameliorate glaucoma in a subject. One of ordinary skill in the art would be able to determine such amounts based on such factors as the subject's size, the severity of the subject's symptoms, and the particular deprenyl compound or route of administration selected.

I. *Deprenyl Compounds*

The language "deprenyl compound", as used herein, includes deprenyl (N,α-dimethyl-N-2-propynylphenethylamine), compounds which are structurally similar to deprenyl, e.g., structural analogs, or derivatives thereof. Thus, in one embodiment, a deprenyl compound can be represented by the following formula (Formula I):

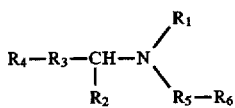 Formula I in which $R_1$ is hydrogen, alkyl, alkenyl, alkynyl, aralkyl, alkylcarbonyl, arylcarbonyl, alkoxycarbonyl, or aryloxycarbonyl;

$R_2$ is hydrogen or alkyl;

$R_3$ is a single bond, alkylene, or —$(CH_2)_n$—X—$(CH_2)_m$;

in which X is O, S, or N-methyl; m is 1 or 2; and n is 0,1, or 2;

$R_4$ is alkyl, alkenyl, alkynyl, heterocyclyl, aryl or aralkyl; and $R_5$ is alkylene, alkenylene, alkynylene and alkoxylene; and $R_6$ is $C_3$–$C_6$ cycloalkyl or —C≡CH; or $R_2$ and $R_4$-$R_3$ are joined to form, together with the methine to which they are attached, a cyclic or polycyclic group;

and pharmaceutically acceptable salts thereof.

In preferred embodiments, $R_1$ is a group that can be removed in vivo. In certain embodiments, $R_1$ is hydrogen. In other preferred embodiments, $R_1$ is methyl. In certain preferred embodiments, $R_2$ is hydrogen. In certain preferred embodiments, $R_2$ is methyl. In some preferred embodiments, $R_3$ is alkylene, more preferably methylene. In other preferred embodiments, $R_3$ is —$(CH_2)_n$—X—$(CH_2)_m$. In preferred embodiments, $R_4$ is aryl. In certain preferred embodiments, $R_4$ is phenyl. In other preferred embodiments, $R_4$ is aralkyl. In yet other preferred embodiments, $R_4$ is alkyl. In still other preferred embodiments, $R_5$ is alkylene, more preferably methylene. In certain preferred embodiments, $R_6$ is

—C≡CH

In other preferred embodiments, $R_6$ is cyclopentyl.

In another preferred embodiment, the deprenyl compound has the structure

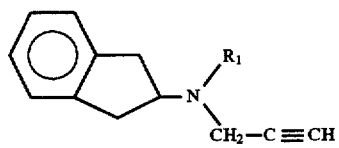

wherein $R_1$ is as described above. In other preferred embodiments, the deprenyl compound is AGN-1133 (N-methyl-N-propynyl-1-indanamine) or AGN-1135 (N-propynyl-1-indanamine). Preferred deprenyl compounds include (–)-deprenyl, (–)-pargyline, (–)-desmethyldeprenyl, and

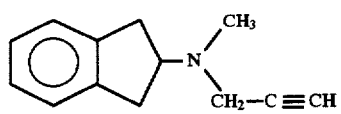

In another embodiment, a deprenyl compound can be represented by the following formula (Formula II):

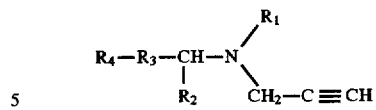 Formula II in which $R_1$ is hydrogen, alkyl, alkenyl, alkynyl, aralkyl, alkylcarbonyl, arylcarbonyl, alkoxycarbonyl, or aryloxycarbonyl;

$R_2$ is hydrogen or alkyl;

$R_3$ is a bond or methylene; and $R_4$ is aryl or aralkyl; or $R_2$ and $R_4$-$R_3$ are joined to form, together with the methine to which they are attached, a cyclic or polycyclic group;

and pharmaceutically acceptable salts thereof.

In another embodiment, the deprenyl compound can be represented by the following formula (Formula III):

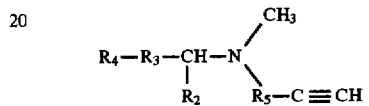 Formula III in which $R_2$ is hydrogen or alkyl;

$R_3$ is a bond or methylene; and $R_4$ is aryl or aralkyl; or $R_2$ and $R_4$-$R_3$ are joined to form, together with the methine to which they are attached, a cyclic or polycyclic group; and $R_5$ is alkylene, alkenylene, alkynylene and alkoxylene;

and pharmaceutically acceptable salts thereof.

In yet another embodiment, the deprenyl compound can be represented by the following formula (Formula IV):

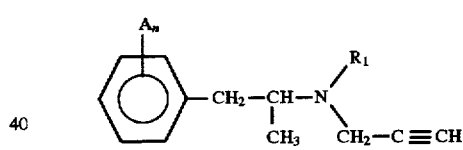 Formula IV in which $R_1$ is hydrogen, alkyl, alkenyl, alkynyl, aralkyl, alkylcarbonyl, arylcarbonyl, alkoxycarbonyl, or aryloxycarbonyl;

A is a substituent independently selected for each occurence from the group consisting of halogen, hydroxyl, alkyl, alkoxyl, cyano, nitro, amino, carboxyl, —$CF_3$, or azido;

n is 0 or an integer from 1 to 5;

and pharmaceutically acceptable salts thereof.

In certain embodiments of the invention, the deprenyl compound is not deprenyl (including (–)-deprenyl).

The term "alkyl" refers to the radical of saturated aliphatic groups, including straight chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 20 or fewer carbon atoms in its backbone (e.g., $C_1$–$C_{20}$ for straight chain, $C_3$–$C_{20}$ for branched chain), and more preferably 10 or fewer. Likewise, preferred cycloalkyls have from 4–10 carbon atoms in their ring structure, and more preferably have 5, 6 or 7 carbons in the ring structure. Unless the number of carbons is otherwise specified, "lower alkyl" as used herein means an alkyl group, as defined above, but having from one to six carbon atoms in its backbone structure. Likewise, "lower alkenyl"

and "lower alkynyl" have similar chain lengths. Preferred alkyl groups are lower alkyls. In preferred embodiments, a substituent designated herein as alkyl is a lower alkyl.

Moreover, the term "alkyl" (or "lower alkyl") as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, carbonyl (such as carboxyl, ketones (including alkylcarbonyl and arylcarbonyl groups), and esters (including alkyloxycarbonyl and aryloxycarbonyl groups)), thiocarbonyl, acyloxy, alkoxyl, phosphoryl, phosphonate, phosphinate, amino, acylamino, amido, amidine, imino, cyano, nitro, azido, sulfhydryl, alkylthio, sulfate, sulfonate, sulfamoyl, sulfonamido, heterocyclyl, aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of aminos, azidos, iminos, amidos, phosphoryls (including phosphonates and phosphinates), sulfonyls (including sulfates, sulfonamidos, sulfamoyls and sulfonates), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The terms "alkenyl" and "alkynyl" refer to unsaturated aliphatic groups analogous in length and possible substitution to the alkyls described above, but that contain at least one double or triple bond respectively.

The term "aralkyl", as used herein, refers to an alkyl or alkylenyl group substituted with at least one aryl group (e.g., an aromatic or heteroaromatic group). Exemplary aralkyls include benzyl (i.e., phenylmethyl), 2-naphthylethyl, 2-(2-pyridyl)propyl, 5-dibenzosuberyl, and the like.

The term "alkylcarbonyl", as used herein, refers to —C(O)-alkyl. Similarly, the term "arylcarbonyl" refers to —C(O)—aryl. The term "alkyloxycarbonyl", as used herein, refers to the group —C(O)—O—alkyl, and the term "aryloxycarbonyl" refers to —C(O)—O—aryl. The term "acyloxy" refers to —O—C(O)—$R_7$, in which $R_7$ is alkyl, alkenyl, alkynyl, aryl, aralkyl or heterocyclyl.

The term "amino", as used herein, refers to —N($R_8$)($R_9$), in which $R_8$ and $R_9$ are each independently hydrogen, alkyl, alkyenyl, alkynyl, aralkyl, aryl, or $R_8$ and $R_9$, together with the nitrogen atom to which they are attached, form a ring having 4–8 atoms. Thus, the term "amino", as used herein, includes unsubstituted, monosubstituted (e.g., monoalkylamino or monoarylamino), and disubstituted (e.g., dialkylamino or alkylarylamino) amino groups. The term "amido" refers to —C(O)—N($R_8$)($R_9$), in which $R_8$ and $R_9$ are as defined above. The term "acylamino" refers to —N($R'_8$)C(O)—$R_7$, in which $R_7$ is as defined above and $R'_8$ is alkyl.

As used herein, the term "nitro" means —$NO_2$; the term "halogen" designates —F, —Cl, —Br or —I; the term "sulfhydryl" means —SH; and the term "hydroxyl" means —OH.

The term "aryl" as used herein includes 5-, 6- and 7-membered aromatic groups that may include from zero to four heteroatoms in the ring, for example, phenyl, pyrrolyl, furyl, thiophenyl, imidazolyl, oxazole, thiazolyl, triazolyl, pyrazolyl, pyridyl, pyrazinyl, pyridazinyl and pyrimidinyl, and the like. Those aryl groups having heteroatoms in the ring structure may also be referred to as "aryl heterocycles" or "heteroaromatics". The aromatic ring can be substituted at one or more ring positions with such substituents as described above, as for example, halogen, azide, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, sulfonamido, ketone, aldehyde, ester, a heterocyclyl, an aromatic or heteroaromatic moiety, —$CF_3$, —CN, or the like. Aryl groups can also be part of a polycyclic group. For example, aryl groups include fused aromatic moieties such as naphthyl, anthracenyl, quinolyl, indolyl, and the like.

The terms "heterocyclyl" or "heterocyclic group" refer to 4- to 10-membered ring structures, more preferably 4- to 7-membered rings, which ring structures include one to four heteroatoms. Heterocyclyl groups include, for example, pyrrolidine, oxolane, thiolane, imidazole, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycyclic group can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "heteroatom" as used herein means an atom of any element other than carbon or hydrogen. Preferred heteroatoms are nitrogen, oxygen, sulfur and phosphorus.

It will be noted that the structure of some of the compounds of this invention includes asymmetric carbon atoms. It is to be understood accordingly that the isomers arising from such asymmetry are included within the scope of this invention. Such isomers are obtained in substantially pure form by classical separation techniques and by sterically controlled synthesis The term "can be removed in vivo", as used herein, refers to a group that can be cleaved in vivo, either enzymatically or non-enzymatically. For example, amides can be cleaved by amidases, and N-methyl amines can be cleaved by enzymatic oxidation. For example, when deprenyl is administered to a subject, it is believed, as described infra, that the methyl group can be removed in vivo to yield an active compound. As a further example, with reference to Formula I, when $R_1$ is alkylcarbonyl, the resulting amide group can be cleaved in vivo to yield a secondary amine (e.g., $R_1$ is converted to hydrogen in vivo). Other groups which can be removed in vivo are known (see, e.g., R. B. Silverman (1992) "The Organic Chemistry of Drug Design and Drug Action", Academic Press, San Diego) and can be employed in compounds useful in the present invention.

II. Pharmaceutical Compositions

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject deprenyl compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The stability of deprenyl can be affected by the pH of the medium in which the deprenyl is formulated. For example, deprenyl is more stable at a pH in the range of about 3–5 than at a pH of about 7. Therefore, when formulating a deprenyl compound in a pharmaceutical composition, it is preferred that the deprenyl compound be maintained at a suitable pH. In preferred embodiments, a pharmaceutical composition of the invention has a pH in the range of about 3 to about 5, more preferably about 3 to about 4. Furthermore, ethyl alcohol is a preferred solvent for improving stability of deprenyl. Thus, in certain embodiments, alcoholic or aqueous alcoholic media are preferred for the pharmaceutical compositions of the invention.

As set out above, certain embodiments of the present deprenyl compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulfonate salts and the like (see, for example, Berge et al. (1977) "Pharmaceutical Salts", *J Pharm. Sci.* 66:1–19).

In other cases, the deprenyl compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the deprenyl compound which produces a therapeutic effect. Generally, out of one hundred per cent, this amount will range from about 0.01 per cent to about ninety-nine percent of active ingredient, preferably from about 0.1 per cent to about 70 per cent, most preferably from about 1 per cent to about 30 per cent.

Methods of preparing these formulations or compositions include the step of bringing into association a deprenyl compound of the present invention with the carrier and, optionally, one or more accessory ingredients. In general, the formulations are prepared by uniformly and intimately bringing into association a deprenyl compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A deprenyl compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered deprenyl compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the deprenyl compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active deprenyl compound, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more deprenyl compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the deprenyl compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a deprenyl compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to a deprenyl compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the deprenyl compound in the proper medium. Absorption enhancers can also be used to increase the flux of the deprenyl compound across the skin. The rate of such flux can be controlled by either providing a rate controlling membrane or dispersing the deprenyl compound in a polymer matrix or gel. Devices, including patches, which transdermally deliver a deprenyl compound by iontophoresis or other electrically-assisted methods can also be employed in the present invention, including, for example, the devices described in U.S. Pat. Nos. 4,708,716 and 5,372,579.

Ophthalmic formulations, eye ointments, powders, solutions, drops, sprays and the like, are also contemplated as being within the scope of this invention.

Pharmaceutical compositions of this invention suitable for parenteral administration comprise one or more deprenyl compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject deprenyl compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given alone or as a pharmaceutical composition containing, for example, 0.01 to 99.5% (more preferably, 0.1 to 90%) of active ingredient in combination with a pharmaceutically acceptable carrier.

The preparations of the present invention may be given orally, parenterally, topically, or rectally. They are of course given by forms suitable for each administration route. For example, they are administered in tablets or capsule form, by injection, inhalation, eye lotion, ointment, suppository, etc.; administration by injection, infusion or inhalation; topical by lotion or ointment; and rectal by suppositories. Injection (subcutaneous or intraperitoneal) or topical ophthalmic administration are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharnaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular deprenyl compound of the present invention employed, or the ester, salt or amide thereof, the route of administration, the time of administration, the rate of excretion of the particular compound being employed, the duration of the treatment, other drugs, compounds and/or materials used in combination with the particular deprenyl compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a deprenyl compound of the invention will be that amount of the compound which is the lowest dose effective to produce a therapeutic effect. Such an effective dose will generally depend upon the factors described above. Generally, intraperitoneal and subcutaneous doses of the compounds of this invention for a patient, when used for the indicated anti-glaucoma effects, will range from about 0.0001 to about 10 mg per kilogram of body weight per day, more preferably from about 0.001 mg/kg to about 1 mg/kg per day.

If desired, the effective daily dose of a deprenyl compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical formulation (composition).

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163, 5,383,851, 5,312,335, 5,064,413, 4,941,880, 4,790,824, or 4,596,556. Examples of well-known implants and modules useful in the present invention include: U.S. Pat. No. 4,487,603, which discloses an implantable microinfusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are well known to those skilled in the art.

It is believed that certain deprenyl compounds can be at least partially metabolized in vivo after administration to a subject. For example, (–)-deprenyl can be metabolized by the liver to (–)-desmethyldeprenyl, as well as (–)-methamphetamine and (–)-amphetamine, after oral administration. The hepatic metabolism of (–)-deprenyl can be inhibited by administration of a $P_{450}$ inhibitor such as Proadifen. In animal and cell-culture studies, administration of Proadifen reduces the ability of (–)-deprenyl to prevent cell death, but does not block the cell-rescuing activity of (–)-desmethyldeprenyl. Thus, it is believed that at least one metabolite of (–)-deprenyl, most likely (–)-desmethyldeprenyl, is an active compound. It is presently believed that (–)-methamphetamine and (–)-amphetamine are inhibitors of the cell-rescuing activity of deprenyl compounds. It is also believed that monoamine oxidase (MAO, including both MAO-A and MAO-B) inhibitory activity is not required for treatment of glaucoma. Absence of MAO inhibitor activity may in fact provide a drug with fewer side effects. Thus, in certain embodiments, it is preferred that the deprenyl compound have low MAO inhibitor activity, or be administered so as to minimize MAO inhibition (e.g., by use of a suitable prodrug or formulation).

In view of the foregoing, it is preferable to administer deprenyl compounds by a route that minimizes metabolism to inhibitor compounds such as (–)-methamphetamine and (–)-amphetamine, while allowing metabolism to active compounds such as (–)-desmethyldeprenyl. Metabolism to an active compound can occur at the desired site of activity, e.g., in the optic nerve. Thus, prodrugs, which are metabolized to active compounds, are useful in the methods of the invention.

It has been found that certain deprenyl compounds have greater therapeutic efficacy (e.g., are effective at lower doses) when administered so as to decrease or prevent the "first-pass" effect. Accordingly, intraperitoneal or especially subcutaneous injection are preferred routes of administration. In preferred embodiments, a deprenyl compound is administered in divided doses. For example, a deprenyl compound can be administered by frequent (e.g., pulsed) injections, or by a controlled infusion, which can be constant or programmably varied as described above. In preferred embodiments in which a deprenyl compound is administered orally, the deprenyl compound can be formulated to reduce the amount of hepatic metabolism after oral administration and thereby improve the therapeutic efficacy.

In certain embodiments, the deprenyl compounds of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs ("targeting moieties"), thus providing targeted drug delivery (see, e.g., V. V. Ranade (1989) *J Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134); gp120 (Schreier et al. (1994)*J. Biol. Chem.* 269:9090); see also K. Keinanen; M. L. Laukkanen (1994) *FEBS Lett.* 346:123; J. J. Killion; I. J. Fidler (1994) *Immunomethods* 4:273. In a preferred embodiment, the therapeutic compounds of the invention are formulated in liposomes; in a more preferred embodiment, the liposomes include a targeting moiety.

The following invention is further illustrated by the following example, which should in no way be construed as being further limiting. The contents of all references, pending patent applications and published patent applications, cited throughout this application are hereby incorporated by reference. It should be understood that the animal model for glaucoma and optical nerve rescue used in the example is accepted and that a demonstration of efficacy in these models is predictive of efficacy in humans.

EXAMPLES

Example
METHODS

All animals were handled according to the Declaration of Helsinki and The Guiding Principles in the Care and Use of Animals. Under halothane/nitrous oxide anaesthesia, two groups of adult Strague-Dawley rats weighing 200–300 gm, eight in each group, were placed in a stereotactic instrument and 1.0 micoliter of 3% Fluoro-Gold (FG, Fluorochrome Inc.), a retrograde tracer, was stereotactically injected bilaterally near to the center of each superior colliculus (Bregma co-ordinates—5.3 mm, 2 mm lateral and 4.5 mm deep). The injections were delivered from a 10 microliter Hamilton syringe over a period of fifteen minutes. Slow injections were used to avoid tissue disruption and the large volume was employed to insure diffusion would extend over the full length of each superior colliculus (SC) (see Tatton et al. ((1991) *Neurosc. Letters* 131, 179–182) for details and rationale of FG injection to pre-label the cell bodies of neurons sending axons to a specific Brian structure).

It has been reported that 40–50% of the neurons whose cell bodies are located in the retinal ganglion cell layer (RGCL) of the rat send an axon to the optic nerve and are RGCs (Cowey et al. (1979) *Exp. Brain Res.* 35, 457–64; Perry V. H. (1981) *Neuroscience* 6, 931–44: and Linden et al. (1989) *Brain Res.* 272, 145–149). The remaining cell bodies in the rat RGCL have been shown to be displaced amacrine cells which do not project to the optic nerve (Perry V. H. (1981) *Neuroscience* 6, 931–44). Most RGCs (>95%) in rats send their axons to the SC with as many as 10% also sending branches to the lateral geniculate body (Cowey et al. (1979) *Exp. Brain Res.* 35, 457–64). Hence the FG injections into the superior colliculus would be expected to retrogradely-label the cell bodies of RGCs projecting to the superior colliculus ($RGC^{SC}$s) but would not label the displaced amacrines in RGCL thereby providing an unambiguous method of $RGC^{SC}$ identification.

Four days were allowed for the retrograde transport of the FG to the $RGC^{SC}$s cell bodies and then the left optic nerve of the rats was exposed and crushed by applying the tips of Dumont number 5 forceps to the nerve immediately behind the globe for ten seconds. Careful attention was used to avoid the central retinal artery. Each nerve was crushed three times at the same site. Following the crushes, the nerve was examined with the aid of an operating microscope to ensure that the axonal component of the nerve was divided into two clearly separated stumps surrounded by an unbroken dural sheath. Retinal artery patency was confirmed by direct ophthalmoscopy.

One group of eight rats received (–)-deprenyl (1 mg/kg) by intraperitoneal (IP) injection every two days for a fourteen day period beginning at the time of optic nerve crush. The remaining group of eight rats received IP injections of saline on the same schedule. Fourteen days after the optic nerve crush all sixteen rats were euthanized with an overdose of somnotol and perfused transcardially with 4% paraformaldehyde in phosphate buffer. The brains and retinas were immersed in 20% sucrose for twenty four hours and then frozen in –70 degrees C. methylbutane. Serial 10 mm sections were cut through the upper brain stem and diencephalon of the animals and viewed under fluorescence microscopy to determine the location and extent of the stereotactic injections of FG. Serial 5 mm sections of the retinas were cut and every third section was Nissl stained. In order to detect even low level FG fluorescence in neuronal cell bodies or processes, the FG labelled brain sections and the retinal sections were examined with the aid of a Hamamatsu intensification camera that allowed the fluorescent images to be digitized using a Matrox frame grabber controlled by image analysis software (Universal Metamorph). This allowed for the creation of computer images of neuronal cell bodies containing FG in the sections taken from areas of the stereotactic injections and sections taken through each of the retinas.

About 25 sections were chosen randomly from the serial sections taken from each retina. Sections were only chosen from the middle 70% of the serial sections where section length exceeded 6 mm. Nissl stained cell bodies in the RGCL were counted at 1000X magnification under oil immersion on a Leitz Orthoplan microscope. RGCL somata were only counted if they contained a well defined nucleus. The cross sectional length of the ganglion cell layer for each section was measured by transferring the retinal section image into a computer using a CCD camera (Dage Ltd.) and IPPLUS 2.1 software (Media Cybernetics). The number of RGCL neuronal cell bodies (RGCLncbs) per mm length of retinal crossection was calculated and were pooled for each of the four lesion/treatment groups (uncrushed-saline, uncrushed-deprenyl, crushed-saline and crushed-deprenyl).

A similar group of sections were randomly chosen from one of the two remaining series of retinal sections. Those sections were lightly Nissl stained and then were mounted in Fluoromount to allow for counts of Nissl stained RGCLncbs under brightfield microscopy and counts of RGCLncbs containing FG under fluorescence microscopy from identical retinal fields. Determination of numbers of RGCLncbs that met the Nissl criteria for neurons and also contained FG were made by switching back and forth from brightfield to fluorescence microscopy. The ratio of the FG containing cell bodies/Nissl stained neuronal somata in each section was used to determine the proportion of RGCLncbs that were $RGC^{SC}$s.

Previous studies have shown that the density of RGCs varies from 1600 per $mm^2$ in the peripheral retina to 2500 per $mm^2$ in some parts near the area centralis (Perry V. H. (1981) *Neuroscience* 6, 931–44). Since the sections that were counted spanned 70% of the width of each retina, they would be expected to include different proportions of the central and peripheral retina. This would result in widely varying RGCL ncbs/mm for different Nissl stained sections and marked differences in the numbers of Nissl stained and FG containing cell bodies that would be identified as $RGC^{SC}$s. Accordingly, the distributions of cell body counts were determined from the pooled values for each experimental group. To determine the statistical significance of any changes in those distributions, the count for each section was treated as a single value and the Kolmogorov-Sminov test (Siegel S. Non-parametric statistics for the behavioral sciences. In: New York: McGraw Hill Book Company, 1956:127–136) was used to compare the values obtained from the four different experimental groups in a pairwise fashion. The Kolmogorov-Smirnov test is a non-parametric test which does not assume an underlying binomial distribution or that the values are linearly related to each other. The method is optimal for comparing widely distributed data (see Ju et al. (*Exp. Neurol.* 126, 233–246) for an example of its use to determine the significance of changes of pooled values taken from large numbers of microscopic sections).

An intensified fluorescent image of a frontal section taken through the SC at 18 days after an injection of FG was examined. Cell bodies and processes in all layers of the SC were found to be labelled with FG. Because of the relatively large injection, FG labelling could be seen over the full rostrocaudal length of both SCs and extended to nearby brainstem and diencephalic structures, including the most caudal portions of the lateral geniculate body. This demonstrated that most, if not all, RGC axons projecting to the SC had taken up FG and transported the fluorescent marker to their retinal cell bodies. Photomicrographs of the same field of a single retinal section viewed alternately under interference contrast microscopy and fluorescence microscopy showed typical $RGC^{SC}$s that were Nissl stained and fluoresced for FG.

FIG. 1 presents box plots of the distributions of the counts of RGCLncbs for the four experimental groups presented with scales showing the counts per section or the percent of cell bodies relative to the mean value found in the uncrushed saline treated group. There was no statistical difference between the distributions for uncrushed saline (48.35±10.75 /mm) and the uncrushed deprenyl (48.39±8.48 /mm) groups (p>0.05). The distribution for the uncrushed saline group was significantly different from the distribution for the crushed saline group (22.70±7.44/mm, p<0.0001) and the distribution for the crushed deprenyl group (32.60±9.94, p<0.01). Importantly, the distribution for the crushed deprenyl group was shifted to significantly greater values than that for the crushed saline group (p<0.001). In short, the numbers of neuronal cell bodies/mm in the RGCL of crushed saline retinas were reduced to an average of 46% of those in uncrushed saline retinae and (−)-deprenyl treatment increased that value to an average of 65%. If, as previously reported, 40–50% of the neurons in the rat RGCL do not send axons to the optic nerve and would not be damaged by the crushes, then these values indicate less than 10% survival for RGCs at fourteen days in the crushed saline retinas and approximately 30–40% survival in the crushed deprenyl retinas.

To determine whether the joint counts of Nissl and FG cell bodies in the RGCL was a reliable estimate of the proportion of RGCs in the layer, the counts of Nissl stained cell bodies and FG labelled cell bodies were plotted as x and y values for varying lengths of retinal sections taken from different portions of the differently lesioned and treated retinas (FIG. 2). The Nissl and FG counts were found to covary linearly independently of section length or location for the uncrushed saline, uncrushed deprenyl, and crushed deprenyl retinal groups with regression coefficients 0.98, 0.96 and 0.90 respectively and y axis intercepts near zero. The slopes did not differ significantly (p>0.05) for the uncrushed saline (0.478±0.021) and uncrushed deprenyl retinal groups (0.379±0.021). The slope of the crushed deprenyl groups (0.219±0.019) was significantly different from the uncrushed saline and uncrushed deprenyl groups (p's<0.0001). Since the counts of FG labelled cell bodies in the crushed saline retinas was very low (average of 0.66/mm), fitting the data to a linear relationship was not valid.

The mean ratios of FG labelled to Nissl stained somata was 0.425±0.045 for the uncrushed saline group, 0.388±0.053 for the uncrushed deprenyl group, 0.003±0.01 for the crushed saline group, and 0.245±0.055 for the crushed deprenyl group. Therefore, by pooling the uncrushed saline and uncrushed deprenyl results, these data estimate that approximately 40.7% of the neuronal cell bodies in the RGCL of retinas with uncrushed optic nerves sent their axons to the SC. These results are consistent with previous reports that 40–50% of the neurons in the rat RGCL are RGCs which send an axon to the optic nerve and that greater than 95% of rat RGCs send axons to the SC.

Figure 3:
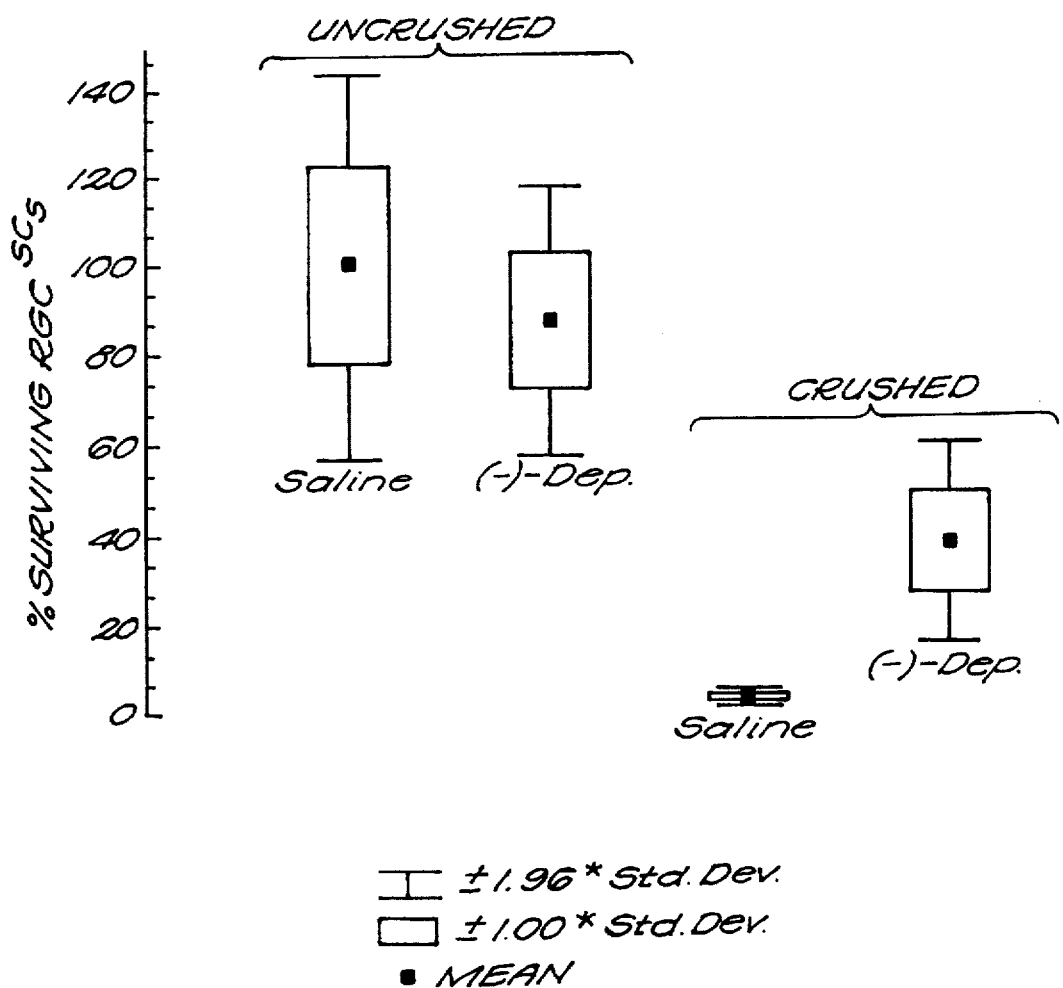
FIG. 3 depicts the distributions of surviving retinal ganglion cells projecting to the superior colliculus ($RGC^{SC}$s) as a percentage of the distribution for uncrushed saline-treated retinas, and showing that deprenyl treatment increases survival of $RGC^{SC}$s after optic nerve crush.

The counts of RGCLncbs and the proportions of FG-labelled cell bodies were combined to determine the distributions $RGC^{SC}$s expressed as percentages of the mean value of the distribution for the uncrushed saline retinas (FIG. 3). There were no significant differences (p>0.05) in the distributions for the uncrushed saline $RGC^{SC}$ group (100.0±22.2%) and the uncrushed (−)-deprenyl $RGC^{SC}$ group (87.0±15.2%). In contrast, crushed saline $RGC^{SC}$ group (3.0±1.0%, p<0.0001) and the crushed (−)-deprenyl $RGC^{SC}$ group (36.9±11.2%, p<0.0001) were distributed differently than the uncrushed saline $RGC^{SC}$ group. The increase in survival in the crushed (−)-deprenyl $RGC^{SC}$ group was significantly different from the crushed saline $RGC^{SC}$ group (p<0.001).

EQUIVALENTS

Those skilled in the art will recognize or be able to ascertain, using no more than routine experimentation, many equivalents to the specific embodiments of the invention described herein. Such equivalents are intended to be encompassed by the following claims.

I claim:

1. A method for treating a subject for glaucoma, comprising:

administering a therapeutically effective amount of a deprenyl compound to a subject such that the subject is treated for glaucoma, wherein the deprenyl compound prevents or delays death of retinal or optic nerve cells and wherein the deprenyl compound is represented by the structure:

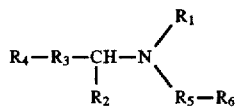

in which $R_1$ is hydrogen, alkyl, alkenyl, alkynyl, aralkyl, alkylcarbonyl, arylcarbonyl, alkoxycarbonyl, or aryloxycarbonyl;

$R_2$ is hydrogen or alkyl;

$R_3$ is a single bond, alkylene, or —$(CH_2)_n$—X—$(CH_2)_m$; in which X is O, S, or N-methyl; m is 1 or 2; and n is 0, 1, or 2;

$R_4$ is alkyl, alkenyl, alkynyl, heterocyclyl, aryl or aralkyl; and $R_5$ is alkylene, alkenylene, alkynylene and alkoxylene; and $R_6$ is $C_3$–$C_6$ cycloalkyl or

and pharmaceutically acceptable salts thereof.

2. The method of claim 1, wherein $R_1$ is a group that can be removed in vivo.

3. The method of claim 1, wherein $R_1$ is hydrogen.

4. The method of claim 1, wherein $R_1$ is alkyl.

5. The method of claim 4, wherein $R_1$ is methyl.

6. The method of claim 1, wherein $R_2$ is methyl.

7. The method of claim 1, wherein $R_3$ is methylene.

8. The method of claim 1, wherein $R_4$ is aryl.

9. The method of claim 1, wherein $R_4$ is phenyl.

10. The method of claim 1, wherein $R_5$ is methylene.

11. The method of claim 1, wherein $R_6$ is

12. The method of claim 1, wherein the deprenyl compound is represented by the structure:

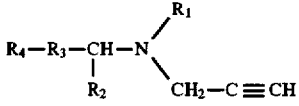

in which $R_1$ is hydrogen, alkyl, alkenyl, alkynyl, aralkyl, alkylcarbonyl, arylcarbonyl, alkoxycarbonyl, or aryloxycarbonyl;

$R_2$ is hydrogen or alkyl;

$R_3$ is a bond or methylene; and $R_4$ is aryl or aralkyl; or $R_2$ and $R_4$–$R_3$ are joined to form, together with the methine to which they are attached, a cyclic or polycyclic group;

and pharmaceutically acceptable salts thereof.

13. The method of claim 1, wherein the deprenyl compound is represented by the structure:

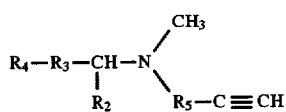

in which

R$_2$ is hydrogen or alkyl;

R$_3$ is a bond or methylene; and

R$_4$ is aryl or aralkyl; or

R$_2$ and R$_4$–R$_3$ are joined to form, together with the methine to which they are attached, a cyclic or polycyclic group; and R$_5$ is alkylene, alkenylene, alkynylene and alkoxylene;

and pharmaceutically acceptable salts thereof.

14. The method of claim 1, wherein the deprenyl compound is represented by the structure:

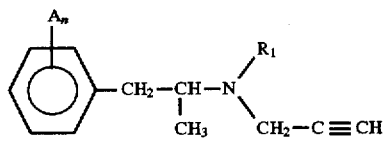

in which

R$_1$ is hydrogen, alkyl, alkenyl, alkynyl, aralkyl, alkylcarbonyl, arylcarbonyl, alkoxycarbonyl, or aryloxycarbonyl;

A is a substituent independently selected for each occurence from the group consisting of halogen, hydroxyl, alkyl, alkoxyl, cyano, nitro, amino, carboxyl, —CF$_3$, or azido;

n is O or an integer from 1 to 5;

and pharmaceutically acceptable salts thereof.

15. The method of claim 1, wherein the deprenyl compound is (–)-deprenyl.

16. The method of claim 1, wherein the deprenyl compound is (–)-pargyline.

17. The method of claim 1, wherein the deprenyl compound is (–)-desmethyldeprenyl.

18. The method of claim 1, wherein the deprenyl compound is administered systemically.

19. The method of claim 17, wherein the (–)-desmethyldeprenyl is administered with a needleless hypodermic injection device.

* * * * *